US00PP36217P2

(12) United States Plant Patent
Klemm et al.

(10) Patent No.: US PP36,217 P2
(45) Date of Patent: Oct. 22, 2024

(54) ***DIANTHUS* PLANT NAMED 'KLEDG20466'**

(50) Latin Name: ***Dianthus* x *allwoodii* Hort.**
Varietal Denomination: KLEDG20466

(71) Applicant: KLEMM + SOHN GMBH & CO. KG, Stuttgart (DE)

(72) Inventors: Nils Klemm, Stuttgart (DE); Lena Thiede, Riederich (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/229,278

(22) Filed: Aug. 2, 2023

(51) Int. Cl.
*A01H 5/02* (2018.01)
*A01H 6/30* (2018.01)

(52) U.S. Cl.
USPC ..... Plt./276

(58) Field of Classification Search
USPC ..... Plt./276, 275, 274
CPC . A01H 5/02; A01H 5/00; A01H 6/305; A01H 6/30
See application file for complete search history.

(56) References Cited

PUBLICATIONS

Upov Pluto 20240130 Dianthus Kledg20466 retrieved on Jan. 30, 2024 at https://pluto.upov.int/result, one page. (Year: 2024).*

* cited by examiner

*Primary Examiner* — June Hwu
(74) *Attorney, Agent, or Firm* — Weatherly IP Solutions, LLC; James M. Weatherly

(57) ABSTRACT

A new *Dianthus* plant designated 'KLEDG20466' particularly distinguished by double light pink flowers and very early flowering, is disclosed.

1 Drawing Sheet

Genus and species: *Dianthus* x *allwoodii* Hort.
Variety denominations: 'KLEDG20466'.

BACKGROUND OF THE NEW PLANT 'KLEDG20466'

The present invention comprises a new and distinct variety of *Dianthus*, botanically known as *Dianthus* x *allwoodii* hort., and hereinafter referred to by the variety name 'KLEDG20466'. 'KLEDG20466' originated from a whole plant mutation from the *Dianthus*parent 'KLEDG12163' (U.S. Plant Pat. No. 24,707) found in an indoor production facility in May 2018 in Stuttgart. Germany.

In September 2018, 'KLEDG20466' was first vegetatively propagated by vegetative stem cuttings in Stuttgart, Germany, and subsequently in Latina, Italy. 'KLEDG20466' was found to reproduce true to type in successive generations of asexual propagation in Stuttgart, Germany and Latina, Italy via vegetative stem cuttings.

SUMMARY OF 'KLEDG20466'

The following are the most outstanding and distinguishing characteristics of 'KLEDG20466' when grown under normal horticultural practices in Stuttgart, Germany.

1. Double, light pink flowers; and
2. Very early flowering.

DESCRIPTION OF THE PHOTOGRAPH

These new *Dianthus* plants are illustrated by the accompanying photograph of plants grown in a greenhouse in Stuttgart, Germany. The colors shown are as true as can be reasonably obtained by conventional photographic procedures.

FIG. 1 shows a whole plant of 'KLEDG20466' showing foliage, buds, and flowers. The photo is of a 30-week-old plant taken in May 2019.

DESCRIPTION OF 'KLEDG20466'

The following detailed descriptions set forth the distinctive characteristics of 'KLEDG20466'. The data which define these characteristics were collected from asexual reproductions carried out in Stuttgart, Germany. Data was collected in May 2019 on 7-month old plants grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus* x *allwoodii* Hort.
- *Common*.—Pot carnation.
- *Designation*.—'KLEDG20466'.

Parentage: Mutation parent is 'KLEDG12163' (U.S. Plant Pat. No. 24,707).

Plant:
- *Propagation type*.—Vegetative cuttings via stem, terminal cuttings.
- *Time to produce a rooted young plant*.—10 to 14 days.
- *Root description*.—Fine roots, young roots are R.H.S. 161D, mature roots are R.H.S. 199C.
- *Rooting habit shape*.—Lanceolate.
- *Plant form*.—Upright.
- *Plant height*.—15 cm to 17 cm.
- *Plant diameter or spread*.—22 cm to 25 cm.

Lateral branches:
*Length*.—7 cm to 10 cm.
*Diameter*.—4 cm to 7 cm.
*Internode length*.—2 cm to 3 cm.
*Number of internodes per branch/stem*.—3 to 5.
*Node length*.—0.2 cm to 0.4 cm.
*Node diameter*.—0.2 cm to 0.4 cm.
*Internode thickness*.—Medium.
*Stem cross section*.—Slightly angular.
*Texture*.—Smooth.
*Color*.—R.H.S. 146B.
*Flowering clusters*.—Some lateral branches.
*Branch/stem appearance in cross-section*.—Solid.

Foliage:
*Arrangement*.—Opposite.
*Length*.—4 cm to 5 cm.
*Width*.—0.3 cm to 0.5 cm.
*Shape*.—Lanceolate.
*Apex*.—Acute.
*Base*.—Obtuse.
*Margin*.—Entire.
*Texture* (*both upper and lower surfaces*).—Smooth.
*Leaf curvature*.—Absent.
*Leaf color*.—Upper surface: R.H.S. 138A for immature leaves and R.H.S. 137A for mature leaves. Lower surface: R.H.S. 138A for immature leaves and R.H.S. 137A for mature leaves.
*Venation pattern*.—Absent.
*Leaf glausity*.—Weak.
*Spiny ciliation of the leaf margin*.—Absent.

Flowers:
*Flower type and habit*.—Semi-double, small sprays, round.
*Fragrance*.—Present.
*Natural flowering season*.—Spring to autumn.
*Position of flowers relative to the foliage*.—Moderately above.
*Number of flowers per spray*.—3 to 5.
*Flower longevity on the plant*.—14 to 18 days.

Buds:
*Length*.—0.5 cm to 1.5 cm.
*Diameter*.—0.3 cm to 0.4 cm.
*Shape*.—Elliptic.
*Color*.—R.H.S. 138A.
*Extrusion of the styles at the bud stage*.—Absent.

Corolla:
*Quantity of petals and arrangement*.—7 to 13 arranged in several whorls.
*Corolla height*.—0.8 cm to 1.5 cm.
*Petal length*.—1.8 cm to 2.5 cm.
*Petal width*.—1.0 cm to 1.5 cm.
*Petal shape*.—Spoon-shaped.
*Petal apex*.—Obtuse.
*Petal base*.—Acute.
*Petal margin*.—Serrated.
*Incision of petal margin*.—Medium.
*Depth of petal margin*.—Shallow.
*Petal texture* (*upper and lower surfaces*).—Smooth.
*Corolla profile of upper part in lateral view*.—Flat convex.
*Corolla profile of lower part in lateral view*.—Flat.
*Petal color*.—Immature: Upper surface: R.H.S. 75C. Lower surface: R.H.S. 75D. Mature: Upper surface: R.H.S. 159 D. Lower surface: R.H.S. 159 D.
*Petal veins color*.—R.H.S. 75A.
*Petal macule*.—Absent.
*Calyx*.—Quantity of sepals and arrangement: Composed of 5 sepals. Shape: Campanulate. Calyx height: 0.8 cm to 1.5 cm. Calyx diameter (at the apex): 0.4 cm to 0.6 cm. Sepal texture (both upper and lower surfaces): Smooth. Sepal color: Upper surface: R.H.S. 137A. Lower surface: R.H.S. 137D. Anthocyanin: Absent.
*Epicalyx*.—Length: 1.0 cm - 1.3 cm. Width: 0.5 cm - 0.7 cm. Outer lobes: Adpressed and free. Apex shapes inner and outer lobes: acute. Color: R.H.S. 137A.

Peduncles:
*Length*.—5 cm to 8 cm.
*Diameter*.—0.2 cm.
*Strength*.—Moderate.
*Texture*.—Smooth.
*Color*.—R.H.S. 146B.

Reproductive organs:
*Stamens*.—Quantity per flower: Moderate. Filament length: 0.5 cm to 0.8 cm. Filament color: R.H.S. 157B. Anther length: 0.1 cm. Anther diameter: 0.05 cm. Anther color: R.H.S. 155B. Pollen amount: Absent.
*Pistils*.—Not observed.

Fruit and seed set: Not observed.

Disease and pest/insect resistance: No disease and pest/insect resistance observed.

COMPARISON OF 'KLEDG20466' WITH PARENTAL LINE AND KNOWN VARIETY

'KLEDG20466' is distinguished from the mutation parent as described in Table 1.

TABLE 1

Comparison with Parental Line

| Characteristic | 'KLEDG20466' | Mutation Parent 'KLEDG12163' |
|---|---|---|
| Main flower color | RHS 75C | RHS 75B |
| Secondary flower color | None | RHS 71A |
| Flower color pattern | Single color | Bi-color |

'KLEDG20466' can be compared to the commercial *Dianthus* variety 'KLEDG18305' (U.S. Plant Pat. No. 31,019). Differences between the varieties are described in Table 2.

TABLE 2

Comparison with Similar Variety

| Characteristic | 'KLEDG20466' | 'KLEDG18305' |
|---|---|---|
| Flower type | Double | Single |
| Flower color | Light pink | Pink with purple ring |
| Flowering time | Very early | Early-medium |

We claim:

1. A new and distinct cultivar of *Dianthus* Plant Named 'KLEDG20466' as described and illustrated herein.

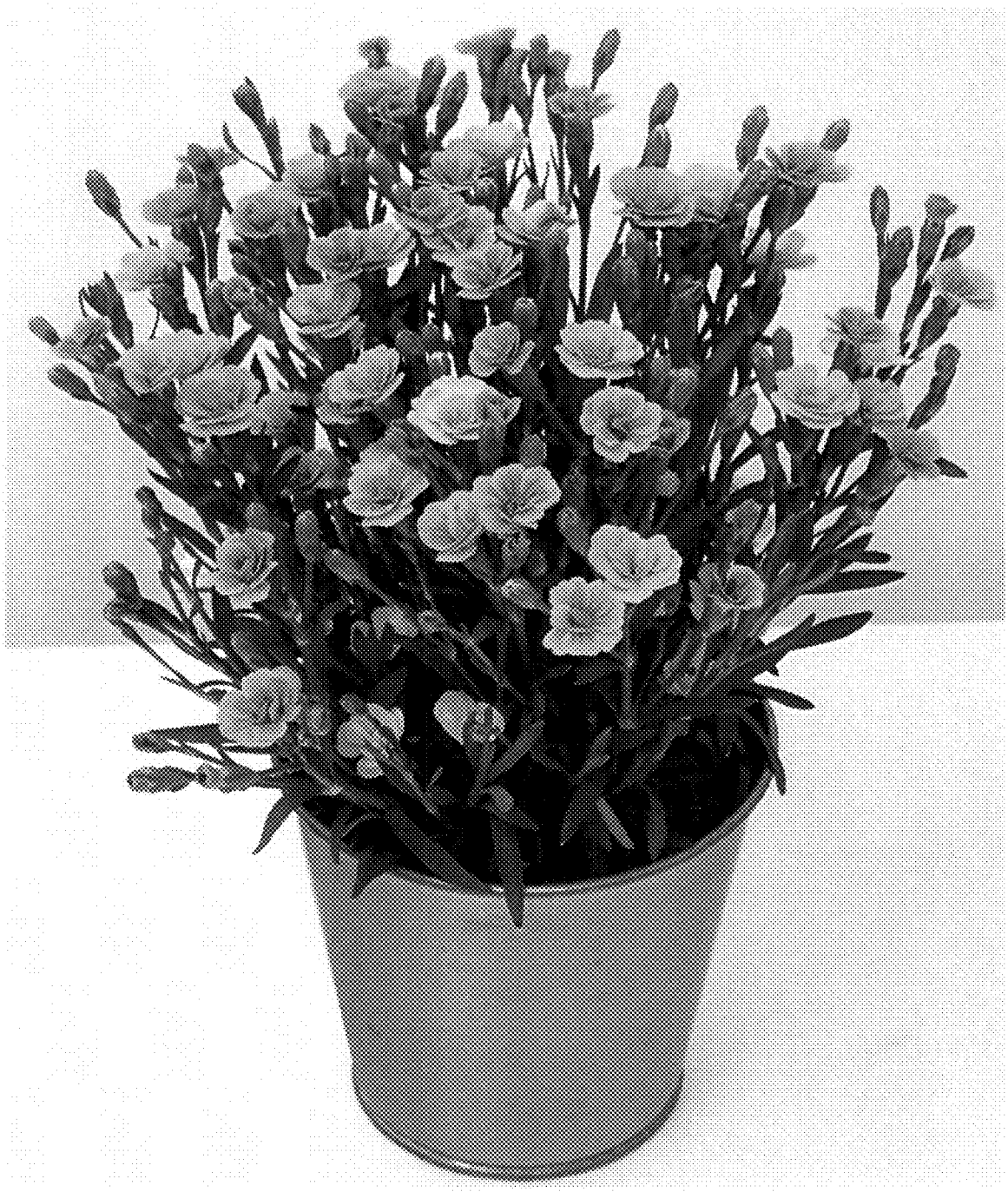

* * * * *